United States Patent
Southerland et al.

(10) Patent No.: US 11,931,364 B2
(45) Date of Patent: *Mar. 19, 2024

(54) MODULATION OF THE NITRIC OXIDE SYNTHASE PATHWAY FOR ORAL HEALTH

(71) Applicant: Meharry Medical College, Nashville, TN (US)

(72) Inventors: Janet H. Southerland, Nashville, TN (US); Pandu R. Gangula, Nashville, TN (US)

(73) Assignee: Meharry Medical College, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/948,184

(22) Filed: Sep. 19, 2022

(65) Prior Publication Data

US 2023/0068887 A1 Mar. 2, 2023

Related U.S. Application Data

(63) Continuation of application No. 16/876,181, filed on May 18, 2020, now abandoned, which is a continuation of application No. 16/213,894, filed on Dec. 7, 2018, now Pat. No. 10,688,098, which is a continuation of application No. PCT/US2017/037031, filed on Jun. 12, 2017.

(60) Provisional application No. 62/349,415, filed on Jun. 13, 2016.

(51) Int. Cl.
| | | |
|---|---|---|
| A61K 31/519 | (2006.01) | |
| A61K 9/00 | (2006.01) | |
| A61K 9/06 | (2006.01) | |
| A61K 9/10 | (2006.01) | |
| A61K 9/68 | (2006.01) | |
| A61P 1/02 | (2006.01) | |
| A61P 5/48 | (2006.01) | |

(52) U.S. Cl.
CPC .......... *A61K 31/519* (2013.01); *A61K 9/0056* (2013.01); *A61K 9/0058* (2013.01); *A61K 9/0063* (2013.01); *A61K 9/06* (2013.01); *A61K 9/10* (2013.01); *A61P 1/02* (2018.01); *A61P 5/48* (2018.01)

(58) Field of Classification Search
None
See application file for complete search history.

(56) References Cited

U.S. PATENT DOCUMENTS

2013/0336945 A1 12/2013 Rustomjee et al.
2016/0136169 A1 5/2016 Perricone

*Primary Examiner* — Celeste A Roney
(74) *Attorney, Agent, or Firm* — Bradley Arant Boult Cummings LLP; Phil Walker; Jessica L. Zurlo

(57) ABSTRACT

Pharmaceutical compositions and methods of treatment or prevention of diseases and conditions associated with or characterized by at least one of xerostomia and periodontal disease by modulation of the nitric oxide synthase pathway are provided, as are animal models and drug screening methods. Such modulation may be achieved by the administration of tetrahydrobiopterin ($BH_4$) or its prodrugs and/or salts. Treating and preventing xerostomia can have the downstream effect of also preventing periodontitis, dental caries, parotid gland enlargement, inflammation and fissuring of the lips (chelitis), inflammation or ulcers of the tongue and buccal mucosa, oral candidiasis, salivary gland infection (sialadenitis), halitosis, and cracking and fissuring of oral mucosa.

20 Claims, 5 Drawing Sheets

MODULATION OF THE NITRIC OXIDE SYNTHASE PATHWAY FOR ORAL HEALTH

CROSS-REFERENCE TO RELATED APPLICATIONS

This application is a divisional of and cites the priority of currently pending U.S. Ser. No. 16/876,181 filed 18 May 2020, which is a continuation of and cites the priority of U.S. Ser. No. 16/213,894 filed 7 Dec. 2018 and issued as U.S. Pat. No. 10,688,098 on 23 Jun. 2020, which is a continuation of and cites the priority of PCT/US17/37031 filed 12 Jun. 2017, which cites the priority of U.S. 62/349,415 filed 13 Jun. 2016. U.S. Ser. No. 16/876,181, U.S. Ser. No. 16/213,894, PCT/US17/37031, and U.S. 62/349,415 are incorporated herein by reference in their entireties.

In this context "government" refers to the government of the United States of America.

STATEMENT REGARDING FEDERALLY SPONSORED RESEARCH

This invention was made with government support under NIH-NIDDK grant number R21DK076704, NIH-NCRR grant number 1U54RR026140-0l, and NIH-NIDCR grant number R01DE020820. The government has certain rights in the invention.

BACKGROUND

A. Field of the Disclosure

The present disclosure relates generally to methods of treatment and/or prevention of diseases and medical conditions, and specifically to those diseases and medical conditions that are associated with or characterized by xerostomia and periodontal disease.

B. Background

Xerostomia, or "dry mouth" is a widespread problem affecting diverse groups of patients. Xerostomia is defined as dry mouth resulting from a change in the amount and/or composition of saliva and often a major oral health complication associated with certain medications, radiation therapy for head and neck cancers, Sjogren's syndrome, and diabetes mellitus. The symptoms of xerostomia range from problems in eating, speaking, swallowing, taste disorders (dysguesia), a painful tongue (glossodynia), and an increased need to drink water. Xerostomia can lead to markedly increasing dental caries, parotid gland enlargement, inflammation and fissuring of the lips (chelitis), inflammation or ulcers of the tongue and buccal mucosa, oral candidiasis, salivary gland infection (sialadenitis), halitosis and cracking and fissuring of oral mucosa.

Diabetes mellitus (DM) is a metabolic disease in which patients' long term prognosis is dependent upon the consistency of their fasting plasma glucose levels remaining below 126 mg/dl. Approximately 29.1 million people are affected by diabetes in the United States. Diabetes mellitus-induced oral health problems are highly prevalent in minority populations particularly African Americans, Latinos and American Indians. DM is thought to promote xerostomia, a qualitative and/or quantitative absence of saliva in the oral cavity.

If left untreated, xerostomia can lead to periodontal disease, with serious health consequences. Periodontal disease contributes to aspiration, pneumonia, heart disease, and poor diabetes control. A lesser known link is the effect poor oral health has on pregnant women which results in preterm low birth weight and increased risk of gingivitis in the mother. Recent studies have also suggested that bacteria originating in the oral cavity from untreated oral disease and infections could spread to the brain and contribute to neurological disorders like dementia. Behaviors that contribute to these conditions include tobacco use, unhealthy diet, overuse of alcohol and poor overall hygiene. An overabundance of bacteria (S. mutans) is responsible for many of these conditions and is avoidable with appropriate dental care.

The physiological relationship between poor oral health and other health problems is well documented and frequently found in low income, uninsured or underinsured, and racial and ethnic minority populations. The past decade has produced a growing number of investigations surrounding the idea that infection and inflammation as a result of oral pathogenesis can lead to the progression of systemic disease. Individuals from minority and underserved backgrounds or who have difficulty accessing essential healthcare services consistently bear a disproportionate amount of disease burden as compared to the other groups. This also means that they will suffer more from complications associated with poor glucose control. Studies have shown that individuals with diabetes who have more severe periodontal disease are at greater risk for cardiovascular and renal disease. An investigation exploring the relationship between oral inflammation and endothelial function demonstrated that periodontitis was associated with endothelial dysfunction in patients with coronary artery disease through a decrease in nitrous oxide (NO) bioavailability (Gangula, Pandu et al. Polybacterial Periodontal Pathogens Alter Vascular and Gut $BH_4$/nNOS/NRF2-Phase II Enzyme Expression, PLoS ONE 10(6): e0129885).

Therefore, there is a need for a readily available treatment for xerostomia that would be accessible to the population groups described above.

SUMMARY

The problems described above, as well as others, are addressed by the following inventions, although it is to be understood that not every embodiment of the inventions described herein will address each of the problems described above. It has been unexpectedly discovered that tetrahydrobiopterin ($BH_4$) treats and prevents xerostomia and periodontal disease.

In a first aspect of the invention, a method of treatment or prevention of a disease or medical condition associated with or characterized by at least one of xerostomia and periodontal disease in a subject is provided, the method comprising administering $BH_4$, a prodrug of $BH_4$, or a pharmaceutically acceptable salt of any of the foregoing to the subject in a therapeutically effective amount.

In a second aspect, a pharmaceutical composition (including a dentifrice) is provided comprising $BH_4$, a prodrug of $BH_4$, or a pharmaceutically acceptable salt of any of the foregoing; and a pharmaceutically acceptable carrier.

In a third aspect, a method of treatment or prevention of a disease or medical condition associated with or characterized by at least one of xerostomia or periodontal disease, is provided, comprising administering the pharmaceutical composition provided above to a subject in need of treatment thereof.

In a fourth aspect, a method of making an animal model of xerostomia is provided, the method comprising administering Streptozotocin to a mammalian subject to induce diabetes mellitus in the subject, and confirming the presence of xerostomia.

In a fifth aspect, a method of screening a candidate drug for a beneficial effect on at least one of xerostomia and periodontal disease is provided, the method comprising administering the candidate drug to a diabetic subject.

In a sixth aspect, a method of screening a candidate drug for a beneficial effect on at least one of xerostomia and periodontal disease is provided, comprising inducing diabetes mellitus in a subject, and administering the candidate drug to the subject.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

A. Definitions

Figure 1A:
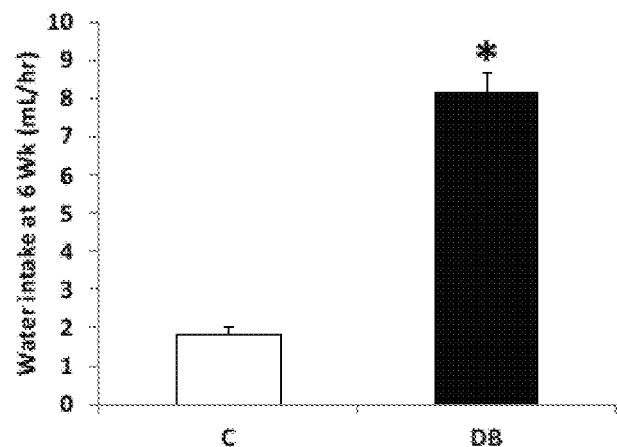
FIGS. 1A-1C. Diabetes induced changes in water intake (see FIG. 1A), induced salivary flow rate (see FIG. 1B), and weight of salivary glands (FIG. 1C) in female rats. The changes in the salivary gravimetry (flow rate; mL/min) and water intake (mL/hr) within the 4 hour period were measured with modifications of the methods originally described by Zaclikevis and hereby incorporated by reference for this teaching (Zaclikevis, M. V. Effects of benzodiazepine and pilocarpine on rat parotid glands: histomorphometric and sialometric study, *Medicinal Chemistry*, 5:74-88). Data were presented 4-6 animals per group. *$p<0.05$, t-test. (n=4 in each group).

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

The terms "prevention", "prevent", "preventing", "suppression", "suppress" and "suppressing" as used herein refer to a course of action (such as implanting a medical device) initiated prior to the onset of a clinical manifestation of a disease state or condition so as to prevent or reduce such clinical manifestation of the disease state or condition. Such preventing and suppressing need not be absolute to be useful.

The terms "treatment", "treat" and "treating" as used herein refers a course of action (such as implanting a medical device) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or device of the present disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or device of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease state or condition. Such effect need not be absolute to be beneficial.

The term "prodrug" as used herein includes functional derivatives of a disclosed compound which are readily convertible in vivo into the required compound. Thus, in the methods of treatment of the present disclosure, the term "administering" shall encompass the treatment of the various disease states/conditions described with the compound specifically disclosed or with a prodrug which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "pharmaceutically acceptable salts" as used herein includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

B. Pharmaceutical Compositions

Nitric oxide (NO) is a non-adrenergic and non-cholinergic neurotransmitter as well as potent vasodilator that plays a key role in salivary gland function and secretion of saliva. Saliva is an essential biological fluid in the body and is predominately produced by three pairs of major salivary glands [Parotid (P), Submandibular (SM), and Sublingual glands (SL)]. Of these, a significant portion of saliva comes from the submandibular gland, which yields over 70% of total saliva production.

The enzyme responsible for in vivo NO biosynthesis is nitric oxide synthase (NOS). 5,6,7,8-tetrahydrobiopterin ("$BH_4$") is a co-factor of NOS for NO biosynthesis. $BH_4$ is synthesized from GTP de novo by the rate-limiting enzyme GCH-1 or from sepiapterin via a salvage pathway by sepiapterin reductase (SR) and dihydrofolate reductase (DHFR) using arginine as a substrate.

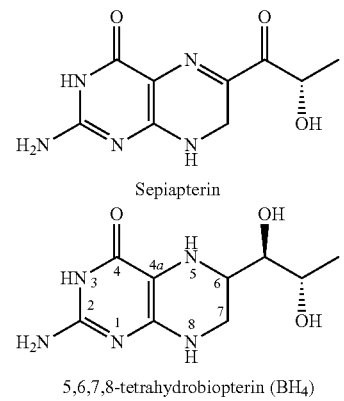

Sepiapterin 5,6,7,8-tetrahydrobiopterin ($BH_4$)

NO is synthesized by three isoforms of NOS. These isoforms include neuronal (nNOS, NOS I), inducible (iNOS, NOS II), and endothelial (eNOS, NOS III), all of which produce NO which functions in different capacities within the central nervous system, immune system, and circulatory system, respectively.

The synthesis of NOS in the salivary glands is regulated by endothelial (e) and neuronal (n) NOS. While eNOS is expressed in the blood vessels and capillaries, nNOS is expressed in nerve fibers surrounding acini of parotid and submandibular salivary glands from many mammalian species as well as surrounding acini from human labial salivary glands.

The activity of NOS depends on the dimerization of two polypeptides aided by $BH_4$. Dimerization results in the creation of high affinity binding sites for $BH_4$ (an NOS cofactor) and arginine (in the oxygenase domain) which enables electron transfer between the flavin and heme groups.

The present disclosure provides for compounds that stimulate NOS activity, either directly or through upregulation of expression, either in vitro or in vivo. The present disclosure also provides for compounds that modulate the activity of a polypeptide regulated by NOS. The present disclosure also provides compounds that indirectly increase NOS activity by either stimulating the activity of a molecule that increases NOS activity or by inhibiting the activity of a molecule that inhibits NOS activity. Such compounds are referred to herein as "active compounds." Such active compounds include, but are not limited to, $BH_4$, sepiapterin, prodrugs of either, and pharmaceutically acceptable salts of any of the foregoing. For the purposes of this disclosure, sepiapterin is considered to be a prodrug of $BH_4$. These active compounds find use in the treatment and prevention of diseases and medical conditions associated with or characterized by at least one of xerostomia and periodontal disease.

Modulating the activity of a polypeptide regulated by NOS as used herein refers to modulating the function of such polypeptide in a manner similar to its regulation by NOS. For example, if NOS stimulates the activity or induces translocation of a given polypeptide, then modulating the activity of such polypeptide refers to stimulating the activity of such polypeptide or stimulating translocation. Likewise, if NOS inhibits the activity or inhibits translocation of a given polypeptide, then modulating the activity of such polypeptide refers to inhibiting the activity of such polypeptide or inhibiting translocation.

Such active compounds can exert their effect on the NOS activity or the activity of a polypeptide regulated by NOS via changes in expression, post-translational modifications or by other means. Suitable active compounds include, but are not limited to, polypeptides, functional nucleic acids, carbohydrates, antibodies, small molecules, or any other molecule which increases the activity of NOS. Such active compounds may be identified in the methods of screening discussed herein.

Unless stated otherwise, all active compounds are to be construed as including a metabolite; such a metabolite may be formed either in vivo within the body or as a result of biochemical activity in vitro. It is within the scope of this disclosure than any active compound may be limited to a non-metabolite compound.

In one embodiment, such active compounds are in the form of compositions, such as but not limited to, pharmaceutical compositions. The compositions disclosed may comprise one or more of such active compounds, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). To form a pharmaceutically acceptable composition suitable for administration, such compositions will contain a therapeutically effective amount of an active compound.

The pharmaceutical compositions of the disclosure may be used in the treatment and prevention methods of the present disclosure. Such compositions are administered to a subject in amounts sufficient to deliver a therapeutically effective amount of the active compound so as to be effective in the treatment and prevention methods disclosed herein. The therapeutically effective amount may vary according to a variety of factors such as, but not limited to, the subject's condition, weight, sex and age. For example, some embodiments of the composition comprise about 3.2 µmol-3.2 mmol of active compound per dosage form. Further embodiments of the composition comprise about 180-640 µmol of active compound per dosage form. A specific embodiment of the composition comprises about 320 µmol of active compound per dosage form. The amount of active compound will in some cases depend on the body mass of the subject. For example, in some embodiments of the composition, the composition comprises about 3.18-635 µmol of active compound per kg body weight per dosage form. In further embodiments, the composition comprises about 15.9-127 µmol of active compound per kg body weight per dosage form. In still further embodiments, the composition comprises about 31.8-63.5 µmol of active compound per kg body weight per dosage form. In specific embodiments, the composition comprises about 31.8 or about 63.5 µmol of active compound per kg body weight per dosage form. Alternatively, the pharmaceutical composition may be formulated to achieve a desired concentration of the active compound to a salivary gland of the subject. In some embodiments of the composition, the composition contains an amount of active agent sufficient to achieve a concentration of 10-1000 µM active agent in a salivary gland of a subject. In a further embodiment, the composition contains an amount of active agent sufficient to achieve a concentration of 50-200 µM active agent at the salivary gland. In a specific embodiment, the composition contains an amount of active agent sufficient to achieve a concentration of 100 µM active agent in a salivary gland of a subject.

Other factors include the mode and site of administration. The pharmaceutical compositions may be formulated to be provided to the subject in any method known in the art. Exemplary routes of administration include, but are not limited to, subcutaneous, intravenous, topical, epicutaneous, oral, intraosseous, intramuscular, intranasal and pulmonary. The compositions of the present disclosure may be formulated to be administered only once to the subject or more than once to the subject. Furthermore, when the compositions are administered to the subject more than once, a variety of regimens may be used, such as, but not limited to, once per day, once per week, once per month or once per year. The compositions may also be formulated to be administered to the subject more than one time per day. The therapeutically effective amount of the active compound and appropriate dosing regimens may be identified by routine testing in order to obtain optimal activity, while minimizing any potential side effects. In addition, formulation for co-administration or sequential administration of other agents may be desirable.

The compositions of the present disclosure may be formulated to be administered systemically, such as by intravenous administration, or locally such as by subcutaneous injection or by application of a gel, fiber, paste or cream.

The compositions of the present disclosure may further comprise agents which improve the solubility, half-life, absorption, etc. of the active compound. Furthermore, the compositions of the present disclosure may further comprise agents that attenuate undesirable side effects and/or decrease the toxicity of the active compound. Examples of such agents are described in a variety of texts, such as, but not limited to, Remington: The Science and Practice of Pharmacy (20$^{th}$ Ed., Lippincott, Williams & Wilkins, Daniel Limmer, editor).

The compositions of the present disclosure can be formulated in a wide variety of dosage forms for administration. For example, the compositions can be in the forms of tablets, capsules, sachets, lozenges, troches, pills, powders, granules, elixirs, tinctures, solutions, suspensions, syrups, ointments, creams, pastes, emulsions, or solutions for intravenous administration or injection. Other dosage forms include for administration transdermally, via patch mechanism or ointment. Further dosage forms include formulations suitable for delivery by nebulizers or metered dose inhalers. Any of the foregoing may be modified to provide for timed release and/or sustained release formulations.

In the present disclosure, the pharmaceutical compositions may further comprise a pharmaceutically acceptable carrier. Such carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, compositions for oral administration in solid form, such as but not limited to, tablets, capsules, sachets, lozenges, troches, pills, powders, or granules, the active compound may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

For oral liquid forms, such as but not limited to, tinctures, solutions, suspensions, elixirs and syrups, the molecules of the present disclosure can be dissolved in diluents, such as water, saline, or alcohols. Furthermore, the oral liquid forms may comprise suitably flavored suspending or dispersing agents such as synthetic and natural gums, for example, tragacanth, acacia, methylcellulose and the like. Moreover, when desired or necessary, suitable coloring agents or other accessory agents can also be incorporated into the mixture. Other dispersing agents that may be employed include glycerin and the like.

The pharmaceutical composition may be a dentifrice. Dentifrices have the advantage of being widely available to consumers. People are therefore familiar with the use of dentifrices, and in most societies apply a dentifrice at least once daily as part of an oral hygiene regime. In addition, dentifrices are effective for the local delivery of active compounds to salivary glands.

The dentifrice may be selected from a group consisting of a paste, a gel, a mouthwash, a powder, and a tooth soap. In some embodiments of the composition, the dentifrice is a paste or gel comprising at least one of an abrasive, a surfactant, a humectant, and a thickener. Such abrasives include but are not limited to hydrated silica, dicalcium phosphate dihydrate, calcium carbonate, sodium bicarbonate, calcium pyrophosphate, and alumina. Such surfactants include but are not limited to sodium lauryl sulfate, sodium N-lauryl sarcosinate, pluronics, sodium lauryl sulfoacetate. Such anticaries agents include but are not limited to fluoride. Such tartar control ingredients include but are not limited to tetrasodium pyrophosphate, Gantrez S-70, sodium tripolyphosphate, and methyl vinyl ether/maleic anhydride copolymer. The dentifrice may further comprise one or more of: water; pH buffers; humectants (to prevent dry-out and increase pleasant mouth feel) such as, but not limited to glycerin, sorbitol, polypropylene glycol, xylitol, and polyethylene glycol; thickeners such as but not limited to silica thickeners, sodium aluminum silicates, and clays; gums such as but not limited to sodium carboxymethyl cellulose, cellulose ethers, xantham gum, carrageenans, sodium alginate, and carbopols; antibacterial agents; flavoring agents such as, but not limited to water-insoluble essential oils; sweetening agents such as, but not limited to saccharin, dextrose, levulose, cyclamate, aspartate; coloring agents; and binders to provide consistency and shape.

For oral administration by mouthwash, the active compound may be combined with one or more of: water and alcohol (such as ethyl alcohol). The mouthwash may further comprise one or more of: surfactants, tartar control ingredients, anticaries agents, buffers, humectants, antibacterial agents, flavoring agents, and coloring agents as described in the preceding section In a specific embodiment, the dentifrice is a powder comprising any of the abrasives described above. The powder may further comprise any of the dry components provided above as suitable in a toothpaste. In another specific embodiment, the dentifrice is a tooth soap comprising one or more of oil and water. The oil may be any that is known to be suitable in a tooth soap, such as, but not limited to olive oil, coconut oil, an essential oil, and peppermint oil.

The pharmaceutical composition may be a chewing gum. The gum may comprise the active compound and a gum, such as butadiene-based synthetic rubber, birch bark tar, chicle, mastic gum, spruce gum, paraffin wax, tolu resin, styrene-butadiene rubber, isobutylene, isoprene copolymer, and petroleum wax. The gum will be present at a concentration sufficient to confer the requisite chewiness to the chewing gum, as could be formulated by one having ordinary skill in the art. Flavorings may be added, including those listed above.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations and in the dentifrice, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include: (a) cationic detergents such as, for example, dimethyldialkylammonium halides, and alkylpyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylene polypropylene copolymers; (d) amphoteric detergents such as, for example, alkylbeta-aminopropionates, and 2-alkylimidazoline quaternary ammonium salts; and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17.

Topical dosage forms, such as, but not limited to, ointments, creams, pastes, and emulsions, containing the active compound, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery, or may be applied to a bandage or dressing for delivery directly to the site of a wound or cutaneous injury.

The active compound of the present disclosure can also be formulated to be administered in the form of liposome delivery systems, such as small unilamellar vesicles, large unilamellar vesicles and antiemtrics. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The active compound of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the active compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

C. Methods of Treatment and Prevention

The teachings of the present disclosure provide for a method of treatment and/or prevention of a disease or medical condition associated with or characterized by at least one of xerostomia and periodontal disease in a subject in need thereof, the method comprising administering any of the active compounds or pharmaceutical compositions disclosed above to the subject in a therapeutically effective amount. Such active compound may be for example $BH_4$, a prodrug of $BH_4$, or a pharmaceutically acceptable salt of either. Conditions associated with or characterized by xerostomia include, but are not limited to, old age, chronic graft-versus-host disease, AIDS, systemic lupus erythematosus, thyroid dysfunction, Parkinson's disease, cerebral palsy, depression, anxiety, post-traumatic stress disorder, dehydration, Eaten-Lambert syndrome, trauma to salivary glands, anorexia, bulimia, Sjogren's syndrome, sarcoidosis, HIV disease, hepatitis C infection, primary biliary cirrhosis, cystic fibrosis, diabetes mellitus, amyloidosis, hemochromatosis, Wegener's disease, salivary gland agenesis (with or without ectodermal dysplasia), and triple A syndrome. Furthermore, some medical treatments are associated with xerostomia. Such medical treatments include, but are not limited to anticholinergic drugs, drugs with sympathomimetic actions, local radiation, and chemotherapy. Anticholinergic drugs that may give rise to xerostomia include, but are not limited to atropine and analogs (antimuscarinics), tricyclic antidepressants, serotonin reuptake inhibitors, antihistamines, antiemetics, and antipsychotics. Drugs with sympathomimetic actions associated with xerostomia include, but are not limited to decongestants, bronchodilators, appetite suppressants, and amphetamines. Other treatments that are also associated with xerostomia include, but are not limited to lithium, omeprazole, oxybutynin, disopyramide, dideoxyinosine, didanosine, diuretics, and protease inhibitors. In some embodiments of the method the subject has undergone or is currently undergoing a medical treatment associated with xerostomia, including but not limited to any of the treatments described above. A further embodiment of the method comprises co-administering a treatment associated with at least one of xerostomia and periodontal disease to the subject, including but not limited to any of the treatments described above.

The method of treatment and/or prevention comprises administering to the subject the active compound in an amount sufficient to treat or prevent at least one of xerostomia and periodontal disease. The method will often further comprise identifying a subject in need of such treatment or prevention. Too little active compound would fail to provide the therapeutic effect. In the case of $BH_4$, lack of $BH_4$ availability leads to enzymatic uncoupling of e/n NOS or reduced NOS dimerization (critical for NOS activity) and lower levels of NO production. On the other hand, excessive $BH_4$ is not optimal because $BH_4$ is an enzyme co-factor involved in other biological pathways, including the degradation of phenylalanine and the biosynthesis of serotonin, melatonin, dopamine, norepinephrine, and epinephrine. Thus, dosing a subject with an excessive amount of $BH_4$ could lead to undesired side-effects.

If, after the administration of the active compound, the subject still has xerostomia or periodontal disease, or is at risk for xerostomia or periodontal disease, then an optional step of the method is to continue administration of the active compound or pharmaceutical composition.

In one embodiment, the method comprises delivering the active compound to a salivary gland of the subject. In the case of $BH_4$, it is desirable to deliver the $BH_4$ to a salivary gland because impaired biosynthesis of salivary gland $BH_4$ accounts for the decrease in NOS activity and NO synthesis in diabetic xerostomia. Supplementation with $BH_4$ may restore e/n NOS protein expression. Targeted delivery to the salivary gland could also prevent unwanted effects on other tissues or organs. In an alternate embodiment, the method comprises administering the active compound locally to the subject's mouth. It is desirable to administer the active compound to the subject's mouth because the salivary glands are in the subject's mouth or very close to the subject's mouth. A specific embodiment comprises administering the active compound locally to the subject's mouth in which the active compound is administered in an oral rinse, a paste, a gel, or a varnish. An oral rinse, a paste, a gel, or a varnish containing active compound would be useful to treat at least one of xerostomia and periodontal disease because these formulations might also contain additives to improve overall oral health (e.g., fluoride). Subjects likely already use similar formulations for routine oral hygiene, so subjects would be more likely to comply with the treatment regimen, leading to better outcomes.

The dosage administered will vary based on the subject in question. For example, some embodiments of the method comprise administering about 3.2 µmol-3.2 mmol of active compound per dose. Further embodiments of the method comprise administering about 180-640 µmol of active compound per dose. A specific embodiment of the method comprises administering about 320 µmol of active compound per dose The dosage administered may depend on the mass of the subject. In one embodiment, the amount of active compound administered is about 3.18-635 µmol of active compound per kg body weight of the subject. As explained previously, the method requires an amount of active compound sufficient to treat or prevent at least one of xerostomia and periodontal disease. In the case of $BH_4$, inadequate dosing of $BH_4$ would not treat or prevent at least one of xerostomia and periodontal disease because an inadequate dose would not provide enough $BH_4$ to induce the dimerization of e/n NOS and the production of NO. An excessive dose could cause off-target effects due to the involvement of active compound in other biological processes. In further embodiments, the amount of active compound administered is 15.9-127 µmol of active compound per kg body weight. In still further embodiments, the amount of active compound administered is about 31.8-63.5 µmol of active compound per kg body weight. In specific embodiments, the amount of active compound administered is about 31.8 or about 63.5 µmol of active compound per kg body weight.

In one embodiment of the method, the amount of active compound administered is effective to achieve a concentration of 10-1000 µM active compound at a salivary gland of the subject. It is desirable to achieve an effective concentration of 10-1000 µM $BH_4$ at a salivary gland because this concentration range of $BH_4$ normalizes NO levels. In a further embodiment of the method, the amount is effective to achieve a concentration of 50-200 µM active compound at the salivary gland of the subject. In a specific embodiment of the method, the amount is effective to achieve a concentration of 100 µM active compound at the salivary gland of the subject.

D. Animal Model and Methods of Screening

The teachings of the present disclosure provide for a method of making an animal model of xerostomia, the method comprising inducing diabetes mellitus in a subject, and confirming the presence of xerostomia in the subject. Xerostomia is a common symptom of diabetes reported in 43% of patients. In this animal model, the classic symptoms of xerostomia may be observed (decreased salivary flow and increased water consumption).

The method may comprise inducing diabetes mellitus by any method known in the art. Diabetes may be induced for example by administering a dose of Streptozotocin (STZ). STZ destroys insulin producing cells (pancreatic β cells) and is known to generate the diabetes phenotype in rats.

The method may comprise confirming xerostomia by any known method, such as measuring at least one of: a salivary flow rate and a water consumption rate of the subject. Decreased salivary flow rate and increased water consumption are classic symptoms of xerostomia in both diabetic and non-diabetic humans. Salivary flow may be measured in the animals by stimulating saliva flow with pilocarpine and measuring the volume of saliva produced. Saliva samples may be collected with the animals placed in ventral decubitus in the operator's hands. Water consumption may be monitored by measuring the volume of water consumed by the animal over a period of time.

The teachings of the present disclosure also provide for a method of screening a candidate drug for a beneficial effect on xerostomia, comprising administering the candidate drug to a diabetic subject. The diabetic subject may be any generally accepted biological model, including a mouse, rat, guinea pig, hamster, rabbit, cat, dog, primate, or human. In a specific embodiment of the method of screening, the diabetic subject is the product of the method of making an animal model of xerostomia described above. The method may further comprise determining the presence or extent of xerostomia after administration. Xerostomia may be diagnosed by any method known in the art, for example by measuring at least one of: a salivary flow rate and a water consumption rate of the subject.

E. Examples

1. Example 1

Induction of Diabetes Mellitus with Streptozotocin (STZ). All procedures were approved by the Institutional Animal Care and Use Committee at Meharry Medical College in accordance with the National Institutes of Health Guide for the Care and Use of Laboratory Animals. Sprague Dawley female rats (9-10 weeks old) arrived at the animal care facility and were held in quarantine for seven days. To eliminate variability in circulating hormonal levels, all experiments were performed in young adult Sprague-Dawley healthy female rats during the diestrus stage of estrus cycle (when circulatory estrogen levels are just beginning to be elevated).

Animals were allowed free access to water and rodent food. Diabetes was induced in rats (n=7) with a single intraperitoneal (55 mg/kg body weight; i.p.) injection of streptozotocin (STZ) in 5 mM citrate buffer, pH 4.0. The control group (n=7) received only citrate buffer. Animals were sacrificed 6 weeks after the STZ injection. To confirm diabetes was induced in the diabetic (DB) animals, blood glucose levels (overnight fasting animals) were obtained 48 hours after STZ injection. Blood (~0.4 µL) was taken from the tail vein, and glucose levels were analyzed using a glucometer. This method for measuring glucose levels was repeated weekly throughout the duration of study. Fasting glucose levels were also obtained from controls. Diabetes was confirmed if blood glucose levels ranged from 300-500 mg/dL. Age-matched control rats demonstrated normal glucose levels ranging from 80-100 mg/dL.

Glucose levels (mg/dL) were significantly increased (DB: 458 f 12.6, Control: 104 f 0.71; p=0.0004) in DB rats, while body weights (grams) were significantly decreased (DB: 252 f 3.87, Control: 282 f 7.99; p=0.744) in DB rats compared to the control group (Table 1).

TABLE 1

Effect of Diabetes on Glucose Levels, Salivary Gland Weights and Xerostomia Symptoms

|  | Control | Diabetes |
|---|---|---|
| Glucose (mg/Dl) | 104 ± 0.71 | 458 ± 12.6* |
| Body Weight (mg) | 282 ± 7.99 | 252 ± 3.87* |
| Water Intake (mL/hour) | 1.81 ± 0.194 | 8.14 ± 0.523* |
| Salivary Flow Rate (mL/min) | 0.235 ± 0.050 | 0.027 ± 0.005* |
| Parotid Gland Weight (mg) | 188 ± 17.2 | 132 ± 13.8* |
| Submandibular Gland Weight (mg) | 445 ± 20.4 | 348 ± 20.7* |
| Sublingual Gland Weight (mg) | 93 ± 29.6 | 85.5 ± 22.9 |

P values less than 0.05 are considered significant and denoted with an (*).
n = 7 in each group.

Control and DB rats were given free access to 250 mL of water for an overnight period of 16 hours. The water intake (mL/hour) was measured at the conclusion of this 16 hour period. Saliva samples were collected after the water intake measurement by applying three drops of 4% pilocarpine hydrochloride into each rat's mouth. Saliva samples were collected with the animals placed in ventral decubitus in the operator's hands. The amount of stimulated saliva collected was measured at the end of an experimental period of 2 minutes. The salivary flow rate was expressed in mL/min.

Figure 1B:
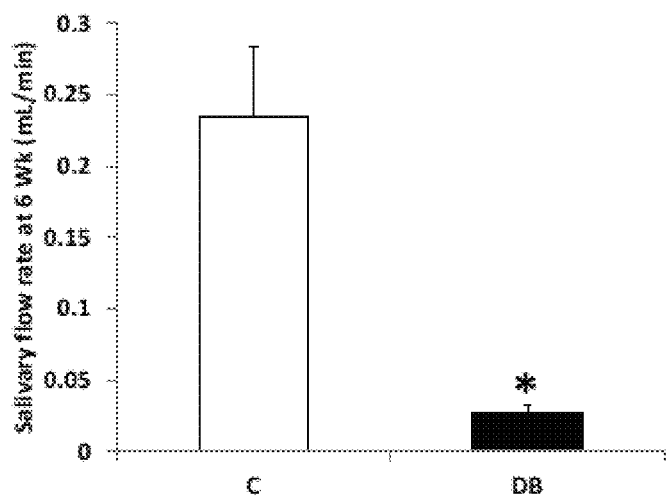
Figure 1C:
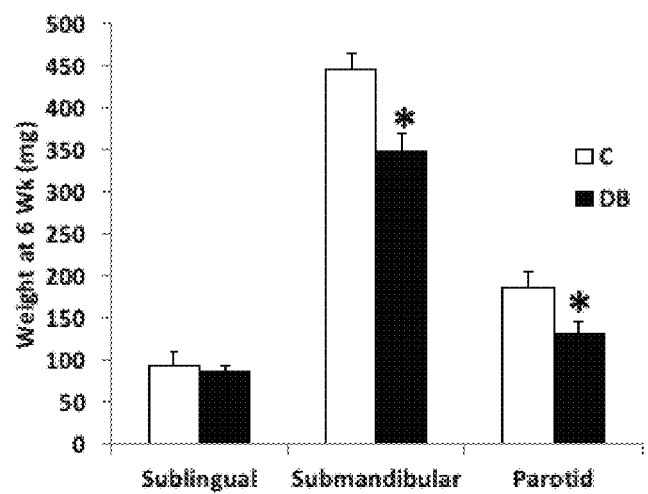

To establish the clinical relevance of our findings we first examined the effects of diabetes on pilocarpine stimulated salivary flow rate as well as water intake in female rats. As shown in FIGS. 1A-1B, diabetes resulted in a delay in increased water intake (FIG. 1A) and increased salivary flow (FIG. 1B) in female DB rats.

2. Example 2

Gland Size Measurements and Western Blotting. Western blot experiments were performed to investigate whether a change in salivary flow rate was due to alterations in salivary gland e/n NOS-α protein expression and dimerization. After rats were sacrificed using $CO_2$, all three pairs of salivary glands were excised from both DB and control rats. Parotid (P), submandibular (SM), and sublingual glands (SL) were placed in pre-weighed vials, weighed, and stored at −80° C. until the samples were subjected to western blotting analysis. In this study, SM glands were used from both the DB and control groups because a significant portion of saliva comes from submandibular glands, producing over 70% of total saliva production. Submandibular glands were homogenized at 4° C. in RIPA lysis buffer. All samples (n=14) were centrifuged at 12,000×g for 20 minutes at 4° C., then the supernatants were separated for protein determinations. Cellular extracts (40 μg protein/lane), positive controls for each enzyme (nNOS, eNOS, GCH-1, DHFR), and molecular weight standards were subjected to 6, 12, and 15% SDS-polyacrylamide gels, respectively. Proteins were then transferred to nitrocellulose membranes and the results were revealed with specific monoclonal antibodies. Changes in specific proteins were normalized with the housekeeping protein, beta-actin. Western blotting and NOS dimerization experiments were performed as previously described and are herein incorporated by reference for that teaching (Gangula P R, Mukhopadhyay S, Ravella K, et al. Tetrahydrobiopterin ($BH_4$), a cofactor for nNOS, restores gastric emptying and nNOS expression in female diabetic rats. *Am J. Physiol. Gastrointest. Liver Physiol.* 2010; 298: G692-G699).

Nitric oxide synthesis enzymes (nNOS, eNOS) and cofactor $BH_4$ biosynthesis enzymes were western blotted and ratios of protein expressions of each enzyme were compared to housekeeping protein, beta-actin. In the case of dimerization, the ratio of monomer and dimer of nNOS and eNOS were analyzed. Trends of increase or decrease were analyzed between nNOS/eNOS and $BH_4$ enzymes to determine if a direct correlation existed between NOS enzymes and $BH_4$ enzymes. Data was presented as mean f standard error (SE). All data was analyzed for statistical comparisons between groups with Student's t-test or Tukey test. P values less than 0.05 were considered significant.

The submandibular (DB: 348 f 20.7, Control: 445 f 20.4; p=0.025) and parotid glands (DB: 132 f 13.8, Control: 188 f 17.2; p=0.048) in diabetic rats weighed significantly less (P<0.05) compared to the control glands. The sublingual glands in diabetic rats also weighed slightly less than control sublingual glands, however, the difference was not found statistically significant (Table 1).

In addition, in diabetic rats, salivary hypofunction correlated with decreased submandibular (SMG) and parotid gland (P) sizes (Table 1). Finally, histology studies demonstrated a disorganized glandular parenchyma with loss of acini limits in diabetic rats (data not shown). The above studies suggest that STZ diabetic rat is a valid model to investigate the proposed experiments.

Figure 3A:
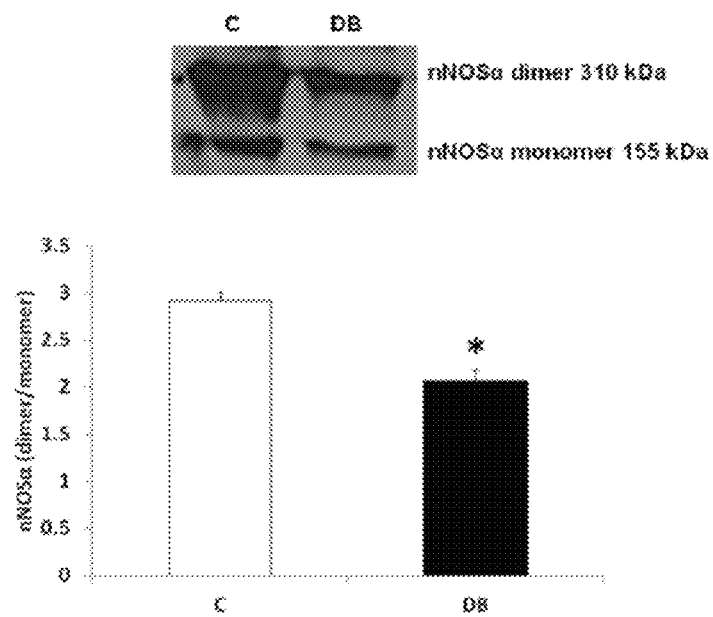
FIGS. 3A-3B. Histogram and immunoblots of submandibular gland homogenates show the ratio of nNOS dimers (FIG. 3A: 310 kDa) to monomers (155 kDa) and eNOS dimers (FIG. 3B: 280 kDa) to monomers (140 kDa). Data are mean f SEM, 4 DB animals and 4 controls. *$p<0.05$ compared to control group (t-test).
Figure 3B:
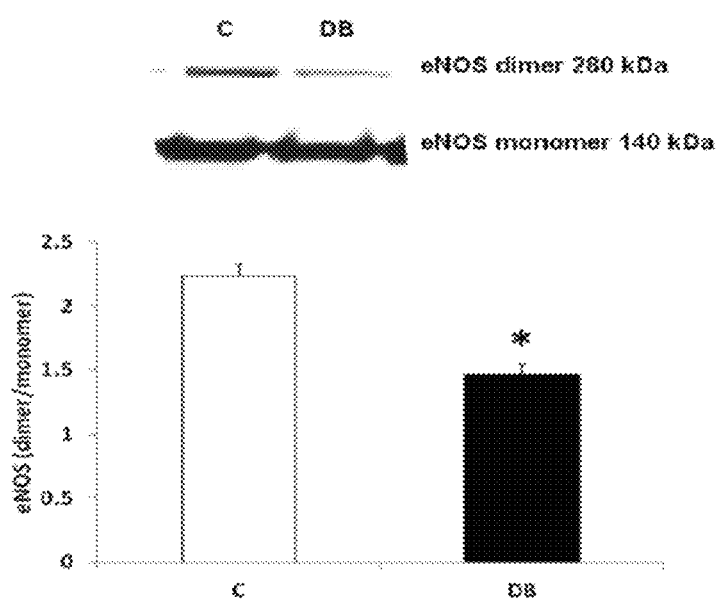
Figure 4A:
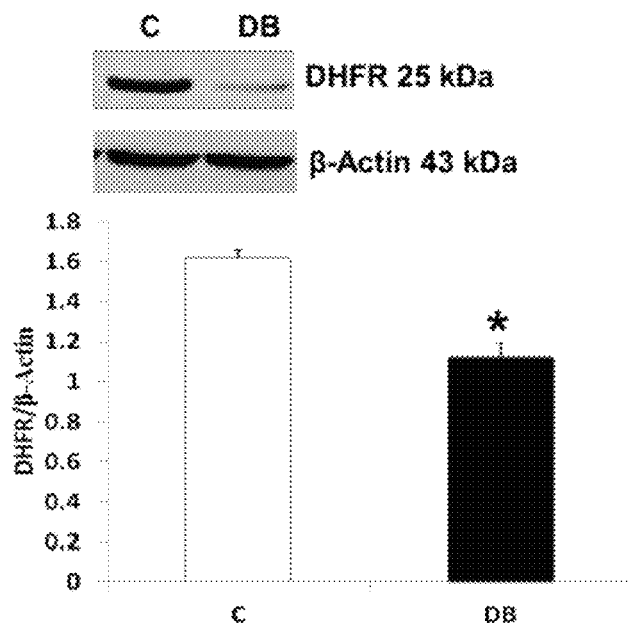
FIGS. 4A-4B. Representative immunoblots of submandibular gland homogenates show the significant decrease in protein expression of DHFR (25 kDa, see FIG. 4A) but not GCH-1 (26 kDa, see FIG. 4B). Also shown are changes in specific proteins normalized to beta-actin levels (housekeeping protein). Data are mean f SEM, 4 DB animals and 4 controls. *$p<0.05$ compared to control group (t-test).
Figure 4B:
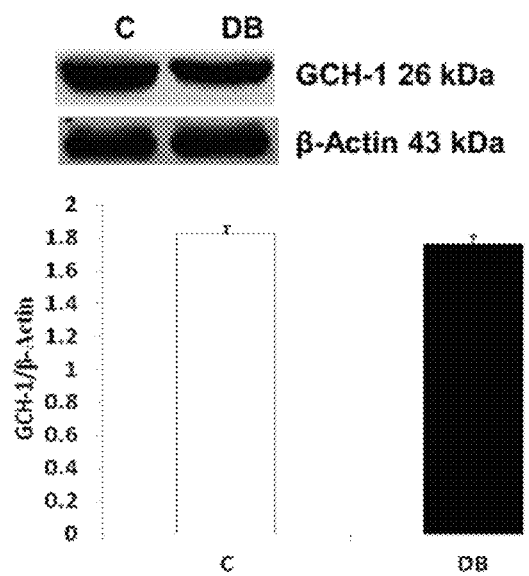

As shown in FIGS. 3A-3B and 4A-4B, both eNOS and nNOS-α protein expression and dimerization were reduced in female diabetic SM glands. SM gland protein expression for both nNOS and eNOS were significantly (P<0.05) decreased in diabetic animals compared to control group (FIGS. 3A-3B). Next, changes in NOS (total) enzyme activity were examined as measured by dimerization of nNOS and eNOS by using low-temperature SDS-PAGE. The results show that the ratio of nNOS and eNOS dimers to monomers was significantly decreased in diabetic rats (P<0.05) compared to control rats (FIGS. 4A-4B). However, these experiments did not reveal whether a reduction in NOS protein was leading to alterations in enzyme activity and NO production in submandibular (SM), parotid (P) and sublingual (SL) glands.

The protein concentration of $BH_4$ biosynthesis enzyme DHFR (salvage pathway) in female control and diabetic SM gland tissues was measured using western blot analysis. As shown in FIG. 5A, significant (p<0.05) reduction in DHFR protein content was seen in SM gland tissues obtained from female diabetic rats. GCH-1 showed a decrease as well, but the change was not statistically significant (FIG. 5B). This data suggests a direct correlation between $BH_4$ biosynthesis via the salvage pathway and a decrease in NOS dimerization.

Discussion. The purpose of this study was to determine the relationship between diabetes, protein expression of NOS isoforms, and $BH_4$ in salivary glands of rats experiencing salivary gland hypofunction and signs of xerostomia.

Chronic Diabetes Leads to Alterations in Salivary Flow and Water Intake

The results from the experiments described in Examples 1-2 suggests another proposed hypothesis for dry mouth seen in diabetic patients that chronic diabetes leads to alterations in salivary flow and water intake. These experiments examined specifically the alteration of protein expression of NOS and $BH_4$ biosynthesis in the salivary glands of diabetic female rats. Xerostomia was confirmed in a DB animal model by observing signs associated with salivary gland dysfunction such as an increase in water intake and decreased saliva production upon pilocarpine-stimulation of DB rats compared to the control counterparts.[12] In the current study, compared to healthy females, DB rats showed a significant decrease in saliva production. Previous studies reported that saliva contains several enzymes and serves as a non-invasive way to measure biological markers for various systemic as well as oral diseases.[15,16,17] The identification of specific enzymes (either absent or in abundance) could reveal further information concerning the adverse clinical manifestations associated with xerostomia.

Chronic Diabetes Impairs eNOS and nNOS Protein Expression and Dimerization in Female Diabetic SM Glands Salivary gland functions are controlled by a number of neuronal and circulatory mechanisms.[18] NO is a non-adrenergic and non-cholinergic neurotransmitter as well as potent vasodilator known to play a key role in salivary gland function and secretion of saliva.[7] Neuronal nitric oxide synthase (nNOS) is expressed in nerve fibers surrounding the acini of the parotid and submandibular salivary glands in many mammalian species as well as surrounding acini in human labial salivary glands.[19,20,21,22,23] Notably, the presence of NOS in human and rodent acinar cells has been demonstrated by functional studies measuring NO synthesis and by determining NOS expression.[7] However, very little information is available on the pathogenesis of NO in human oral diseases. The expression of nNOS was shown to be reduced in NOD animal models similar to Sjogren's syndrome (SS), a chronic autoimmune rheumatic disease characterized by a severe dryness of the mouth and other mucosal tissues.[7] The present studies showed that We NOS protein expression and dimerization were altered in female diabetic rat SM glands. This suggests that the NOS mechanisms in salivary gland hypofunction, regardless of its etiology, can be generalized among various causes associated with xerostomia. Furthermore, the animal model established in this study can be used as a tool to investigate the underlying mechanisms that may be associated with salivary gland disfunction and thus development of xerostomia in the onset of diabetes. Previous research in humans have shown that salivary flow rate is reduced in the onset of diabetes mellitus.[3,4] In the current study, it was found that the salivary volume and weights of all three salivary glands (P, SM, SL) were reduced in the diabetic rat compared to controls. However, only the P and SM glands displayed a significant difference. Thus further research is needed to examine other potential mechanisms that may impair NO pathways as well as impede function of the salivary glands.

Chronic Diabetes Reduces $BH_4$ Biosynthesis in SM Glands of Female Diabetic Rats Tetrahydrobiopterin deficiency leads to We NOS uncoupling and reduced enzyme activity; We NOS activity represents a critical signaling node for regulating salivary gland function.[25] The catalytic activity of We NOS depends on a dimerization step, aided by $BH_4$.[9,25] $BH_4$ is synthesized from GTP de novo by the rate-limiting enzyme GCH-1 or from a salvage pathway (via dihydrofolate reductase, DHFR) using arginine as a substrate.[9,25] The present study showed that DHFR protein expression ($BH_4$ biosynthetic enzyme via salvage pathway) was reduced in SM glands of 6 week diabetic female rats.

Reduction in submandibular gland DHFR protein expression correlated well with altered We NOS protein expression and dimerization in female diabetic rats. The alterations in $BH_4$-NO synthesis are correlated with decreased salivary flow rate and increased water intake a classic symptom of xerostomia in diabetic and non-diabetic humans.[7,8,36] Examining more definitive time points in the onset of xerostomia along with $BH_4$-mediated NO signaling and salivary function will provide a more complete understanding of the role of $BH_4$-NO pathway in diabetes-induced xerostomia. Further, it may help to develop new chemotherapeutic compound(s) to treat signs and symptoms of xerostomia in diabetic patients.

Figure 2A:
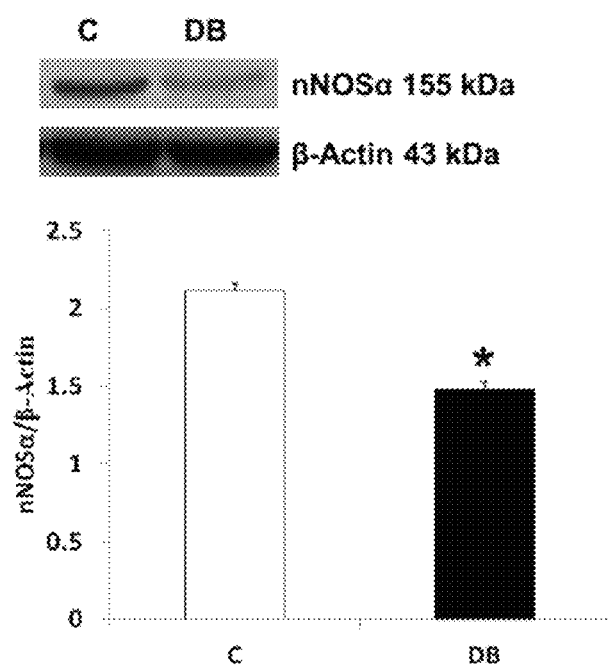
FIGS. 2A-2B. Histogram and immunoblots of submandibular homogenates showing the decrease in protein expression of nNOS (155 kDa) (FIG. 2A) and eNOS (140 kDa) (FIG. 2B) female diabetes (DM) when compared to female control (C). Also shown are changes in specific proteins normalized to beta-actin (house-keeping protein). Data are mean f SEM, 4 DB animals and 4 controls. *$p<0.05$ compared to control group (t-test).
Figure 2B:
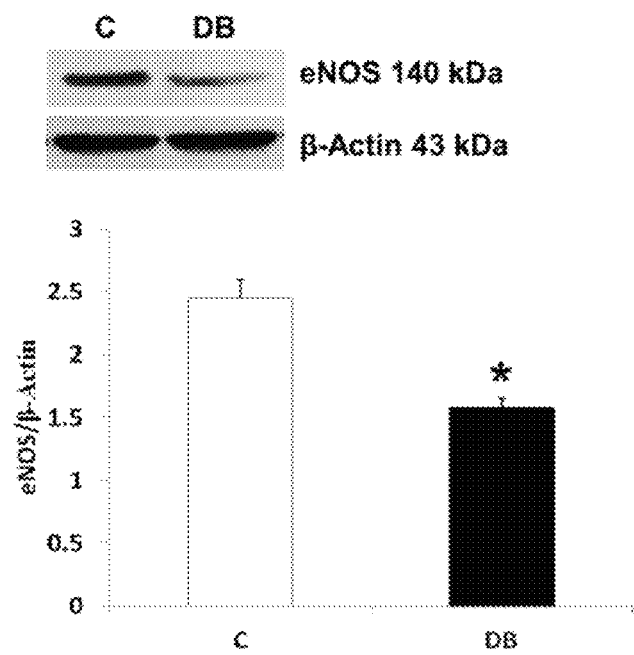
Figure 5:
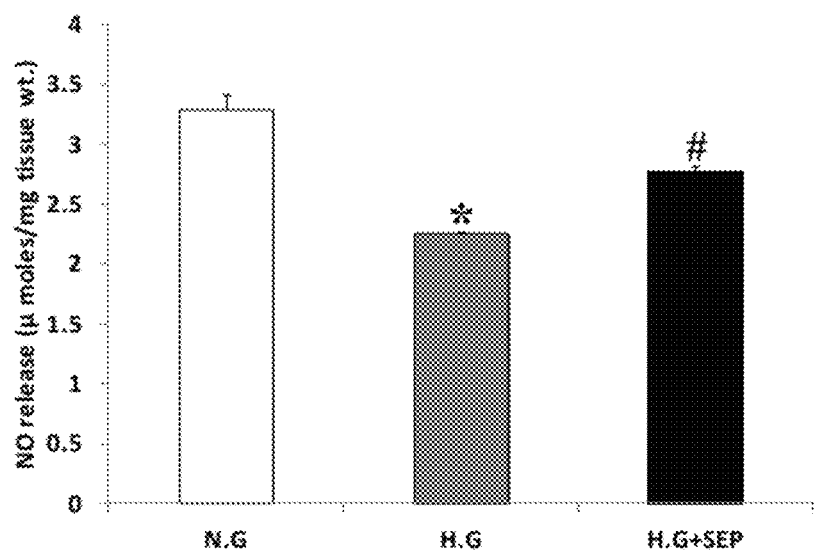
FIG. 5. Effect of hyperglycemia (55 mM, 48 hr incubation) and supplementation of sepiapterin (SEP, 100 μM), on nitric oxide release in rat tissue. The bars represent mean f SEM. *$p<0.05$ non-glycemic (N.G, Control) vs. hyperglycemic (H.G); #$p<0.05$ N.G vs. SEP, t-test (n=4 in each group).

Sepiapterin Supplementation Restores Impaired e/n NOSα Dimerization, NO Synthesis and Saliva Secretion Experimental data indicates that e/n NOSα protein expression was reduced in female diabetic SM gland tissues compared to control group (FIGS. 2A-2B). Protein expression for DHFR was reduced in diabetic female rats (FIGS. 3A-3B). In-vitro supplementation of sepiapterin improved NO release in the tissue exposed to hyperglycemia (FIG. 5). All the above findings correlated well with the impaired saliva secretion and water intake (FIGS. 1A-1B) and e/n NOS activity (FIGS. 3A-3B) as measured by dimerization in SM gland tissue. Therefore, dietary supplementation of sepiapterin improves e/n NOSα dimerization, nNOS activity, NO synthesis and saliva secretion.

Notably, dietary $BH_4$ has been shown to be useful and safe in improving endothelium-dependent relaxation in patients with diabetes gastroparesis[28], patients with type II diabetes[37], chronic smokers[38], hypercholesterolemia[39], as well as venous conduits used for coronary artery bypass graft surgery.[40] Future studies will be highly significant because they will help delineate the role of NO in the pathogenesis of xerostomia in a diabetic rat model and determine if $BH_4$ supplementation in vivo ameliorates any observed exocrine defects.

References for Examples

1. Diabetes: Symptoms, Causes, and Treatments, 2015-Available at http://www.medicalnewstoday.com/info/diabetes/(last visited January 2015).
2. Statistics about Diabetes, Data from the National Diabetes Statistics Report, 2014—Available at http://www.diabetes.org/diabetes-basics/statistics/#sthash.Ck6Y0yP6.dpu. (last visited January 2015).
3. Gandara B K, Morton T H. Non-periodontal oral manifestations of diabetes: a framework for medical care providers. *Diabetes Specar* 2001; 24:199-205.
4. Sreebny L M, Yu A, Green A, et al. Xerostomia in diabetes mellitus. *Diabetes Care* 1992; 15:900-904.
5. Fazzi, M, Vescovi, P, Savi, A, et al. *The effects of drugs on the oral cavity. Minerva stomatol* 1999; 48 (10): 485-492.
6. Wijers O B, Levendag P C, Braaksma M M, et al. Patients with head and neck cancer cured by radiation therapy: a survey of the dry mouth syndrome in long-term survivors. *Head & Neck* 24 2002; (8): 737-747.
7. Rosignoli F, Goren N B, Leiros C P. Alterations in nitric oxide synthase activity and expression in submandibular glands of NOD mice. *Clin Immunol* 2001; 101:86-93.
8. Looms D, Tritsarls K, Pederson A M, et al. Nitric oxide signaling in salivary glands. *J Oral Pathol Med* 2002; 31:569-584.
9. Thony B, Auerbach G, Blau N. Tetrahydrobiopterin biosynthesis, regeneration and functions. *Biochem J* 2000; 347 Pt 1:1-16.
10. Gorren A C, Schrammel A, Schmidt K, et al. Thiols and neuronal nitric oxide synthase: complex formation, competitive inhibition, and enzyme stabilization. *Biochemistry* 1997; 36: 4360-4366.
11. Gangula P R, Mukhopadhyay S, Ravella K, et al. Tetrahydrobiopterin (BH4), a cofactor for nNOS, restores gastric emptying and nNOS expression in female diabetic rats. *Am J Physiol Gastrointest Liver Physiol* 2010; 298: G692-G699.

12. Zaclikevis M V, D'Agulham A C, Bertassoni L E, et al. Effects of benzodiazepine and pilocarpine on rat parotid glands: histomorphometric and sialometric study. *Med Chem* 2009; 5:74-88.
13. Tucker A S, Miletich I. Salivary glands: development, adaptations and disease. In: *Frontiers of Oral Biology*, Basel: 2010 Karger Publisher; Vol 14, 98-106.
14. Nanci, A, Salivary Glands In: *Ten' Cates Oral Histology: Development, Structure, and Function, 8$^{th}$ Edition*. Saint Louis: 2012. Mosby; (11):253-295.
15. Bartels C L. Xerostomia: Helping patients with dry mouth. The oral cancer foundation. 2014. Available at http://www.oralcancerfoundation.org/complications/xerostomia.php. (Last Modified May 2014, Accessed on Jul. 10, 2014).
16. Koscielniak D, Jurczak A, Zygmunt A, et al. Salivary proteins in health and disease. *Acta Biochim Pol* 2012; 59:451-457.
17. Schafer C A, Schafer J J, Yakob M, et al. Saliva diagnostics: utilizing oral fluids to determine health status. *Monogr Oral Sci* 2014; 24:88-98.
18. Proctor G B, Carpenter G H. Regulation of salivary gland function by autonomic nerves. *Autonomic Neuroscience: basic and clinical* 2007; 133:3-18.
19. Alm P, Ekstrom J, Larsson B, et al. Nitric oxide synthase immunoreactive nerves in rat and ferret salivary glands and effects of denervation. *Histochem J* 1997; 29:669-676.
20. Lohinai Z, Szekely A D, Soos L, et al. Distribution of nitric oxide synthase containing elements in the feline submandibular gland. *Neurosci Lett* 1995; 192:9-12.
21. Soinila S, Vanhatalo S, Lumme A, et al. Nitric oxide synthase in the autonomic and sensory ganglia innervating the submandibular salivary gland. *Microsc Res Techn* 1996; 35:32-43.
22. Takai N, Uchihashi K, Higuchi K, et al. Localization of neuronal-constitutive nitric oxide synthase and secretary regulation by nitric oxide in the rat submandibular and sublingual glands. *Arch Oral Biol* 1999; 44:745-750. Klatt P, Schmidt K, Werner E R, et al. Determination of nitric oxide synthase cofactors: heme, FAD, FMN, and tetrahydrobiopterin. *Methods Enzymol* 1996; 268:358-365.
23. Wang D, Yuan Z, Inoue N, et al. Abnormal subcellular localization of AQP5 and downregulating AQP5 protein in parotid glands of streptozotocin-induced diabetic rats. *Biochim Biophys Acta*. 2011; 1810(5):543-554.
24. Okada D. Tetrahydrobiopterin-dependent stabilization of neuronal nitric oxide synthase dimer reduces susceptibility to phosphorylation by protein kinase C in vitro. *FEBS Lett* 1998; 434:261-264.
25. Moens A L, Kass D A. Therapeutic potential of tetrahydrobiopterin for treating vascular and cardiac disease. *J Cardiovasc. Pharmacol* 2007; 50: 238-246.
26. Schmidt T S, Alp N J. Mechanisms for the role of tetrahydrobiopterin in endothelial function and vascular disease. *Clin Sci* 2007; 113: 47-63.
27. Gangula P R, Mukhopadhyay S, Pasricha P J, et al. Sepiapterin reverses the changes in gastric nNOS dimerization and function in diabetic gastroparesis. *Neurogastroenterol Motil* 2010; 22:1325-1331.
28. Klatt P, Schmidt K, Uray G, et al. Multiple catalytic functions of brain nitric oxide synthase. biochemical characterization, cofactor-requirement, and the role of N omega-hydroxy-L-arginine as an intermediate. *J Biol Chem* 1993; 268:14781-14787.
29. Kuzkaya N, Weissmann N, Harrison D G, Dikalov S, et al. Interactions of peroxynitrite, tetrahydrobiopterin, ascorbic acid, and thiols: implications for uncoupling endothelial nitric-oxide synthase. *J Biol Chem* 2003; 278: 22546-22554.
30. Cai S, Alp N J, McDonald D, et al. GTP cyclohydrolase I gene transfer augments intracellular tetrahydrobiopterin in human endothelial cells: effects on nitric oxide synthase activity, protein levels and dimerisation. *Cardiovasc Res* 2002; 55:838-849.
31. Sartoretto J L, Kalwa H, Pluth M D, et al. Hydrogen peroxide differentially modulates cardiac myocyte nitric oxide synthesis. *Proc Natl Acad Sci* 2011; 108:15792-15797.
32. Meininger C J, Marinos R S, Hatakeyama K, et al. Impaired nitric oxide production in coronary endothelial cells of the spontaneously diabetic BB rat is due to tetrahydrobiopterin deficiency. *Biochem J* 2000; 349:353-356.
33. Meininger C J, Cai S, Parker J L, et al. GTP cyclohydrolase I gene transfer reverses tetrahydrobiopterin deficiency and increases nitric oxide synthesis in endothelial cells and isolated vessels from diabetic rats. *FASEB J* 2004; 18:1900-1902.
34. Nguyen L, Pasricha P J. Sapropterin improves gastric accommodation and symptoms in women with diabetic gastroparesis. *Neurogastroenterol Motil* 2013; 25 (suppl) 1:13-45.
35. Katoh S, Sueoka T. Development of tetrahydrobiopterin and GTP cyclohydrolase in salivary glands of rats. *Int J Biochem* 1986; 18:131-135.
36. Heitzer T, Krohn K, Albers S, et al. Tetrahydrobiopterin improves endothelium dependent vasodilation by increasing nitric oxide activity in patients with type II diabetes mellitus. *Diabetologia* 2000; 43: 1435-1438.
37. Heitzer T, Brockhoff C, Mayer B, et al. Tetrahydrobiopterin improves endothelium-dependent vasodilation in chronic smokers: evidence for a dysfunctional nitric oxide synthase. *Circ Res* 2000 86: E36-E41.
38. Stroes E, Kastelein J, Cosentino F, et al. Tetrahydrobiopterin restores endothelial function in hypercholesterolemia. *J Clin Invest* 1997; 99: 41-46.
39. Maier W, Cosentino F, Lutolf R B, et al. Tetrahydrobiopterin improves endothelial function in patients with coronary artery disease. *J Cardiovasc Pharmacol* 2000; 35: 173-178.
40. Nederofers T. Xerostomia and hyposalivation. *Adv Dent Res* 2000; 14:48-56.

F. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

We claim:

1. A method of treating or reducing the likelihood of xerostomia in a subject, the method comprising administering a pharmaceutical composition to the subject, the pharmaceutical composition comprising:
an agent selected from tetrahydrobiopterin ($BH_4$), a prodrug of $BH_4$, or a pharmaceutically acceptable salt of any of the foregoing, in a therapeutically effective amount.

2. The method of claim 1, wherein the prodrug of $BH_4$ is sepiapterin.

3. The method of claim 1, wherein the administering comprises delivering the pharmaceutical composition to a salivary gland of the subject.

4. The method of claim 1, wherein the administering comprises delivering the pharmaceutical composition locally to the mouth of the subject.

5. The method of claim 1, wherein the pharmaceutical composition is formulated for oral administration.

6. The method of claim 1, wherein the pharmaceutical composition is formulated as a paste, a gel, a mouthwash, a powder, a tooth soap, a gum, a film, a spray, or a lozenge.

7. The method of claim 1, wherein the agent is present in an amount of from about 31.8 µmol to about 63.5 µmol per kg weight of the subject.

8. The method of claim 1, wherein the agent is present in an amount of from about 3.2 µmol to about 3200 µmol of the pharmaceutical composition.

9. The method of claim 1, wherein the amount of the agent is effective to achieve a concentration of 10-1000 µM of $BH_4$ at a salivary gland of the subject.

10. The method of claim 1, wherein the subject is suffering from or at risk of at least one of xerostomia or decreased salivary flow.

11. The method of claim 1, further comprising treating or reducing the likelihood of at least one of dental caries, parotid gland enlargement, inflammation of the lips, fissuring of the lips, inflammation of the tongue, ulcers of the tongue, inflammation of the buccal mucosa, ulcers of the buccal mucosa, oral candidiasis, salivary gland infection, halitosis, or cracking of oral mucosa.

12. A method of treating or reducing the likelihood of xerostomia in a subject, the method comprising administering a pharmaceutical composition to the subject, the pharmaceutical composition comprising:
a dentifrice, gum, film, spray, or lozenge; and
an agent selected from tetrahydrobiopterin ($BH_4$), a prodrug of $BH_4$, or a pharmaceutically acceptable salt of any of the foregoing, in a therapeutically effective amount.

13. The method of claim 12, wherein the prodrug of $BH_4$ is sepiapterin.

14. The method of claim 12, wherein the administering comprises delivering the pharmaceutical composition to a salivary gland of the subject.

15. The method of claim 12, wherein the administering comprises delivering the pharmaceutical composition locally to the mouth of the subject.

16. The method of claim 12, wherein the pharmaceutical composition is formulated for oral administration.

17. The method of claim 12, wherein the agent is present in an amount of from about 31.8 µmol to about 63.5 µmol per kg weight of the subject.

18. The method of claim 12, wherein the agent is present in an amount of from about 3.2 µmol to about 3200 µmol of the pharmaceutical composition.

19. The method of claim 12, wherein the amount of the agent is effective to achieve a concentration of 10-1000 µM of $BH_4$ at a salivary gland of the subject.

20. The method of claim 12, further comprising treating or reducing the likelihood of at least one of decreased salivary flow, dental caries, parotid gland enlargement, inflammation of the lips, fissuring of the lips, inflammation of the tongue, ulcers of the tongue, inflammation of the buccal mucosa, ulcers of the buccal mucosa, oral candidiasis, salivary gland infection, halitosis, or cracking of oral mucosa.

* * * * *